(12) United States Patent
Raju et al.

(10) Patent No.: US 8,252,010 B1
(45) Date of Patent: Aug. 28, 2012

(54) THROMBECTOMY REMOVAL METHOD

(76) Inventors: Seshadri Raju, Jackson, MS (US);
Peter Neglen, Brandon, MS (US)

( * ) Notice: Subject to any disclaimer, the term of this patent is extended or adjusted under 35 U.S.C. 154(b) by 0 days.

(21) Appl. No.: 13/289,139

(22) Filed: Nov. 4, 2011

Related U.S. Application Data

(62) Division of application No. 12/510,778, filed on Jul. 28, 2009, now Pat. No. 8,057,497.

(51) Int. Cl.
*A61B 17/22* (2006.01)
(52) U.S. Cl. .......................................... 606/159; 604/22
(58) Field of Classification Search .................. 606/127, 606/128, 159, 200; 604/22, 103.01, 103.02, 604/500
See application file for complete search history.

(56) References Cited

U.S. PATENT DOCUMENTS 5,250,060 A * 10/1993 Carbo et al. .................. 606/159
5,462,529 A * 10/1995 Simpson et al. ......... 604/101.04

* cited by examiner

*Primary Examiner* — Victor Nguyen
(74) *Attorney, Agent, or Firm* — Jones, Walker, Waechter, Poitevent, Carrere & Denegre, LLP

(57) ABSTRACT

A method for removing a clot using and inserting a catheter balloon assembly, having proximal and distal ends including a catheter carrying a remotely inflatable occlusion balloon and another catheter carrying a mechanical device for moving a clot, into patient on one side of clot; a balloon-collared sheath, having a collar sheath with proximal and distal ends, the collar sheath having an open interior, and sealing valve for sealing the interior of the collar sheath, and inflatable collar balloon, disposed on the exterior distal end of said collar sheath, inserted on other side of clot; a suction module, having a suction sheath having proximal and distal ends, the suction sheath having an open interior, and sized to be inserted in a vein, attachable to a suction device. The balloons are inflated and the mechanical device is positioned near the clot, toward the balloon collared sheath towards the suction device.

10 Claims, 8 Drawing Sheets

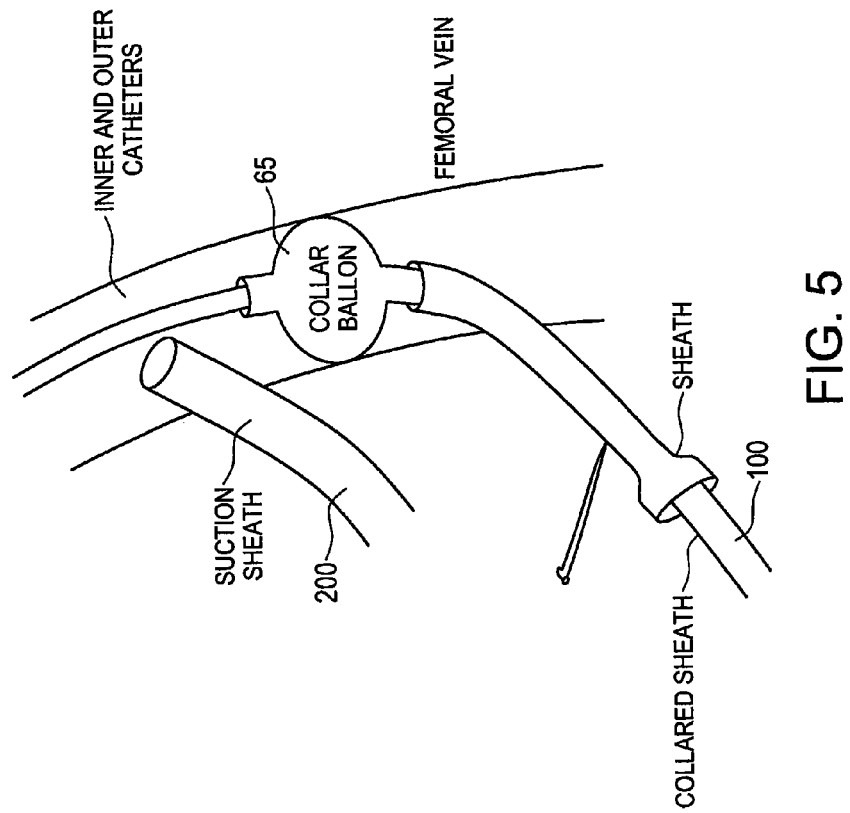

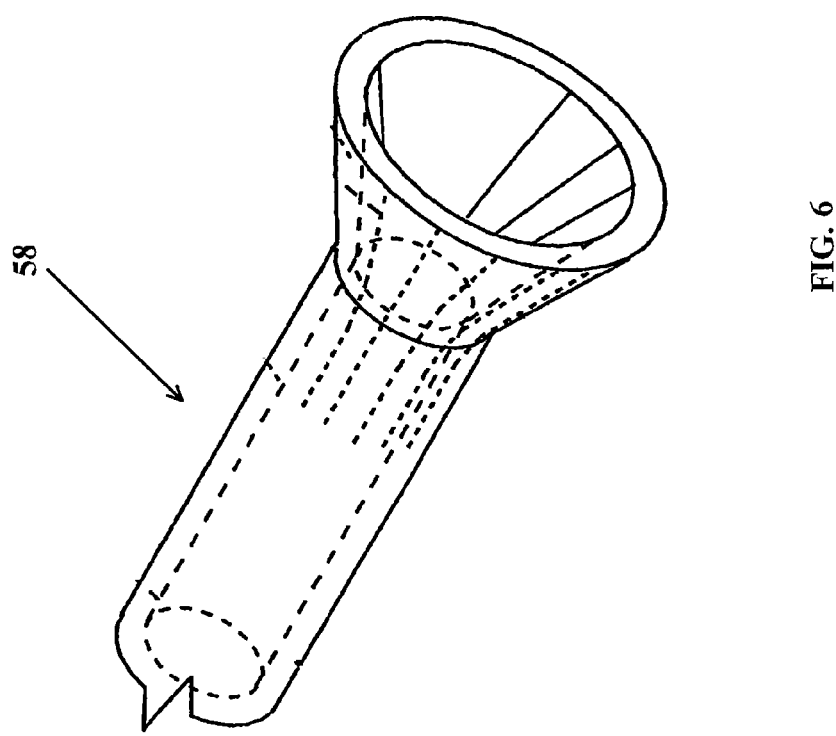

THROMBECTOMY REMOVAL METHOD

PRIORITY CLAIM

This application is a divisional of U.S. application Ser. No. 12/510,778, filed Jul. 28, 2009, which has been given projected U.S. Pat. No. 8,057,497 to be issued on Nov. 15, 2011, and claims the priority benefit thereof.

FIELD OF INVENTION

The invention relates to devices for removing early stage blood clots, or late stage blood clots within stents.

BACKGROUND OF THE INVENTION

Acute venous thrombosis (also referred to as acute deep venous thrombosis (DVT)) is a condition where blood clots (thrombosis) form inside veins. An acute clot is initially soft (jelly-like). The vessel and surrounding tissue will respond with an inflammatory reaction and over weeks and months the clot will become "hardened" and retract and partially obstruct the lumen. Classic symptoms of acute venous thrombosis include pain, swelling and redness of the leg and dilation of the surface veins. However, these symptoms may be absent in certain cases. The traditional treatment for venous thrombosis, in its early jelly-like stage, is to use blood thinners (anticoagulation) without removing the clot itself (anticoagulants often do not actively dissolve the clot, but prevent new clots from forming).

Removal of the thrombus in addition to anticoagulation is beneficial to long term patency. Currently, there are two main approaches to remove the clot in the early stage (generally, within 14 days of onset of symptoms): (1) dissolution or lysis of the clot by administering a clot dissolving enzyme (a lytic agent) through a catheter into the vein harboring the clot; or (2) removal of the clot by a mechanical device, sometimes priming the clot with a lytic agent prior to removal. In the "hardened" late stage (sometimes referred to as post-thrombotic disease), thrombectomy is generally ineffective, and the condition is generally treated with balloon angioplasty and possible stenting.

Currently available mechanical devices include the AngioJet (Possis Medical, Inc., Minneapolis) and the Trellis, manufactured by Bacchus Vascular, Inc., Santa Clara, Calif.

The AngioJet is a dual lumen catheter designed to rapidly remove blood clots with minimal vascular trauma. The AngioJet System is typically used in conjunction with thrombolytics. The Trellis is a drug infusion device designed for isolated thrombolysis. A thrombus is isolated between two occlusion balloons while the thrombolytic is mechanically dispersed with an oscillating wire and then aspirated.

Currently available mechanical thrombectomy devices perform poorly without lytic agents as their mechanical efficiency is poor. However, use of lytic agents poses the risk of inducing bleeding into normal tissues leading to serious complications such as stroke. Additionally, mechanical removal of clots presents the potential for embolism when portions of a clot break off and migrate to undesired locations. A new mechanical design is intended to improve clot removing efficiency without the need to employ a lytic agent and to reduce the occurrence of embolism.

SUMMARY OF THE INVENTION

BRIEF DESCRIPTION OF THE DRAWINGS

FIG. 1A is a perspective view of the end of the catheter assembly showing the two balloons inflated.

FIG. 5 is a cartoon depiction showing the suction sheath and balloon collared sheath positioned in a patient's vein.

FIG. 6 is a prospective view of one embodiment of an expandable cone used to move a lesion or clot.

DESCRIPTION OF THE PREFERRED EMBODIMENT

Figure 1:
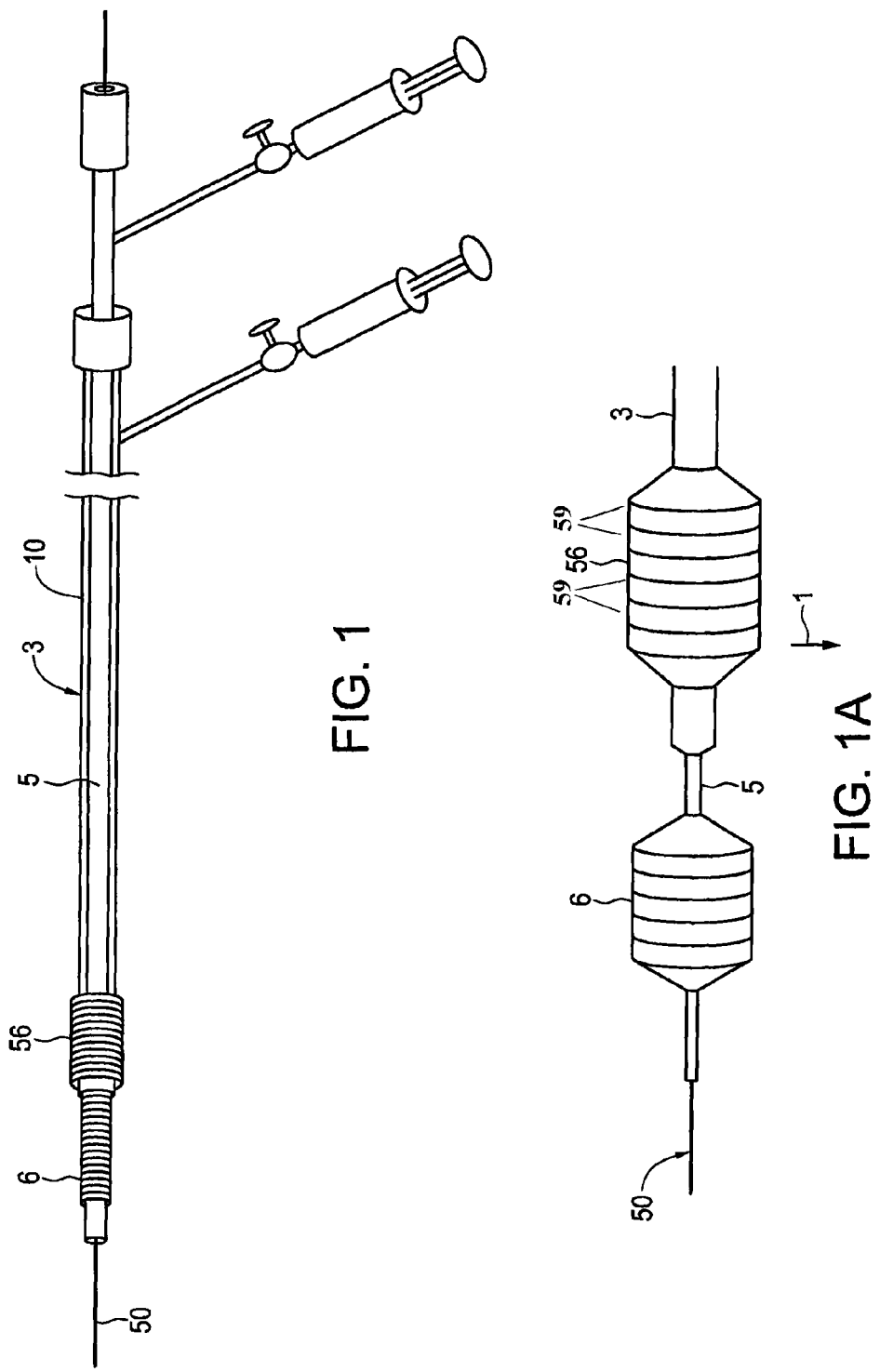
FIG. 1 is a partial cutaway view of one embodiment of a balloon catheter assembly.
Figure 2:
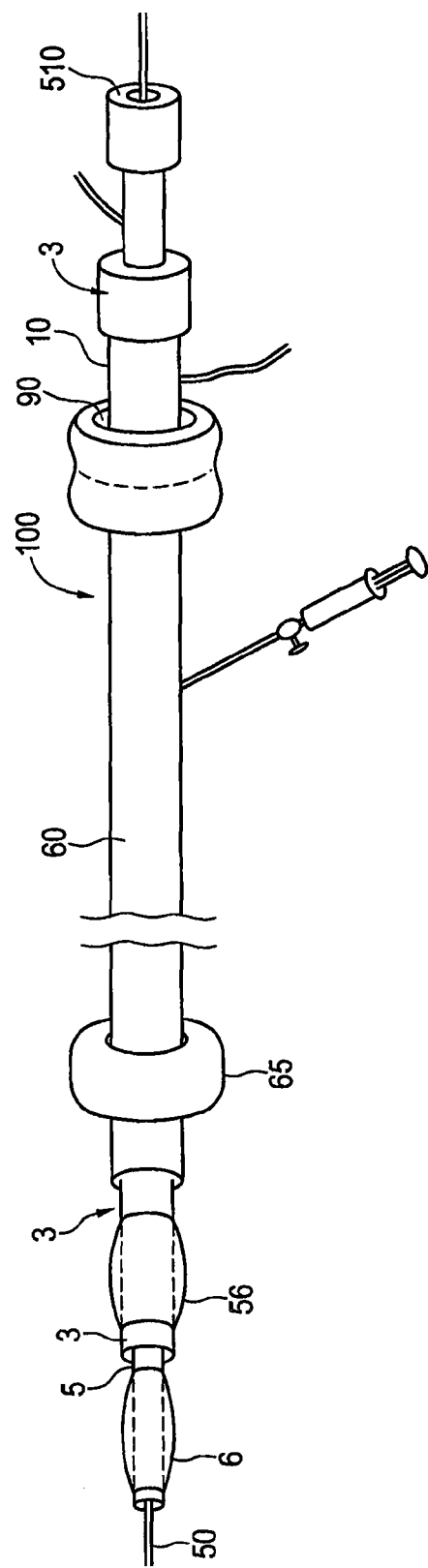
FIG. 2 is a perspective view of one embodiment of the balloon module.
Figure 2A:
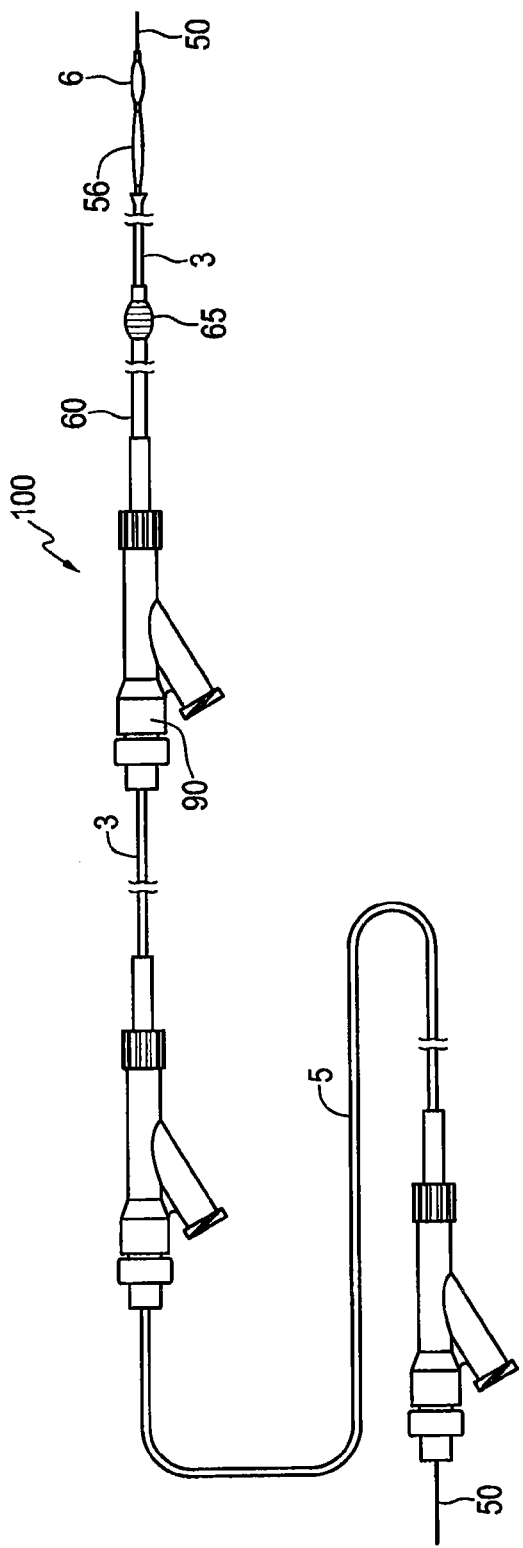
FIG. 2A is a schematic showing the relationship of the various modules.
Figure 3:
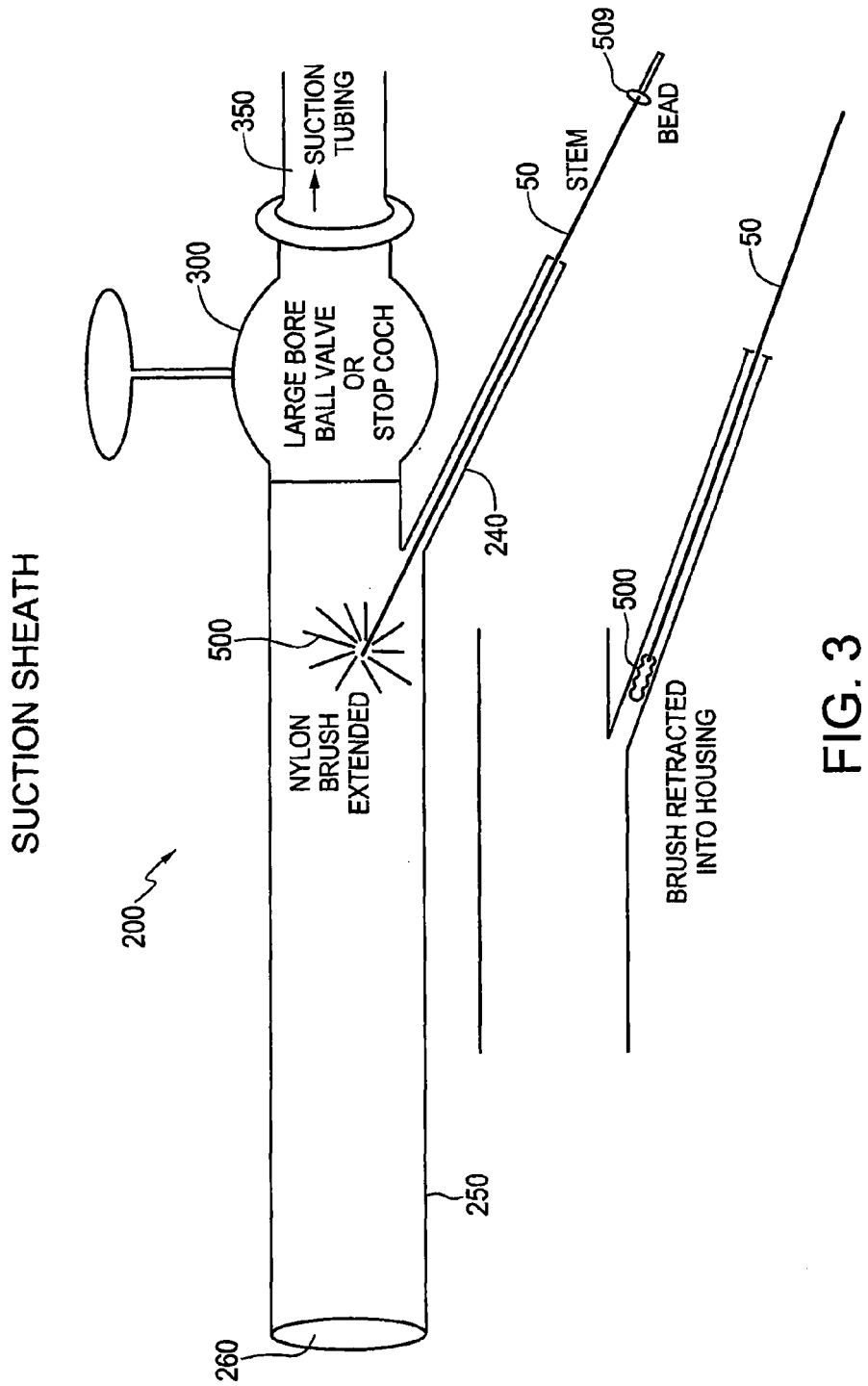
FIG. 3 is a perspective view of one embodiment of the suction sheath module.
Figure 3A:
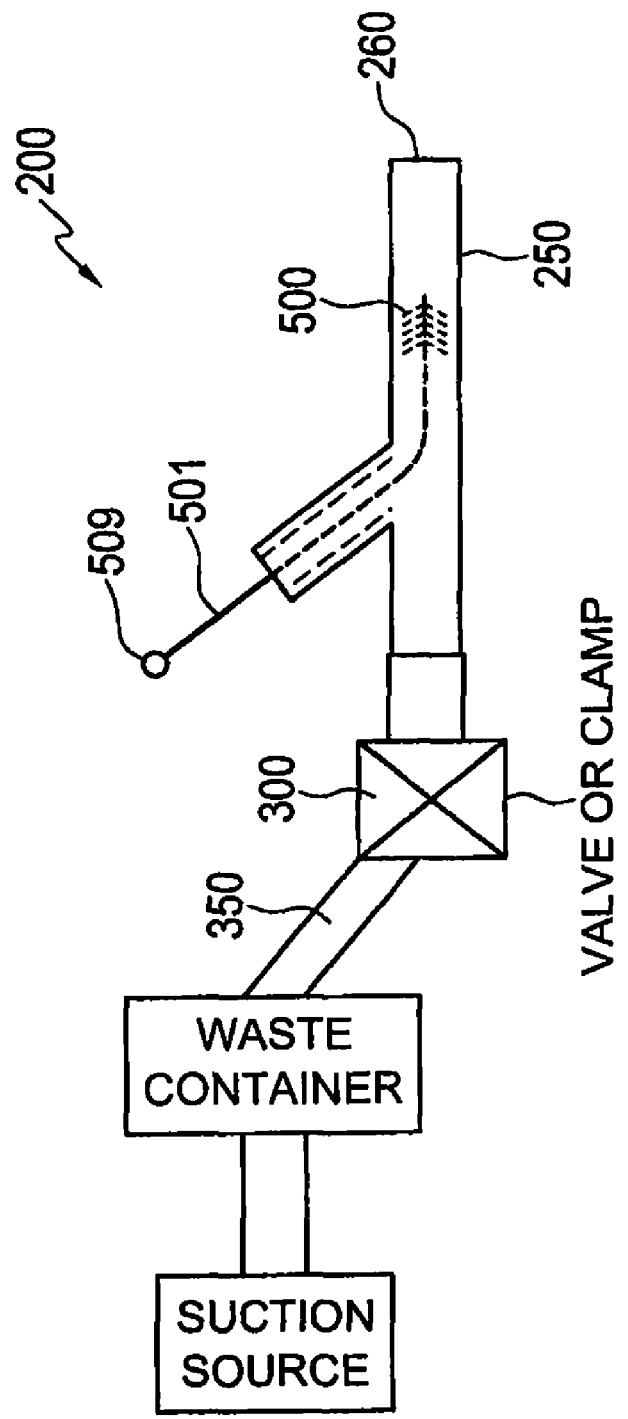
FIG. 3A is a depiction of one embodiment of the suction sheath module parts.

The kit device comprises three modules, a catheter balloon assembly 3, depicted in FIG. 1; a balloon module 1, depicted in FIG. 2; and a suction module 200, depicted in FIG. 3. As the catheter assembly 3 is inserted through the balloon module 100 in use, the catheter assembly will be described as part of the balloon module, although they are separate devices.

The Balloon Module

The balloon module 1 comprises a deployment balloon-collared sheath 100 (FIG. 2), and a catheter balloon assembly 3 comprising a hollow inner catheter 5 and a hollow outer catheter 10, where the inner catheter 5 is slidable in the outer catheter 10's interior, in a nested relationship (one inside the other), and slidable on a deployment guide wire. Catheter and catheter sheath construction is well known in the art as can be seen in U.S. Pat. No. 7,220,269, hereby incorporated by reference, and U.S. patent application number 2008/0275393, hereby incorporated by reference. Sheaths and catheters are tubular structures with a central lumen, and have been manufactured with flexible plastic-type materials, having high hoop strengths or with reinforcements, to help stop kinking and bending while reducing tissue damage. Braided polyurethane with wire reinforcement has been used, as well as for example, as described in Hillstead U.S. Pat. No. 5,066,285, the tubular sheath of a catheter sheath introducer is made of expanded, fibrous polytetrafluoroethylene (PTFE) so as to produce a more flexible sheath having a high hoop strength that resists kinking. Also, as described in Kocak U.S. Pat. Nos. 4,634,432 and 4,705,511, the tubular sheath of a catheter sheath is made with a reinforcing helical spring molded into the sheath material so as to provide a flexible tube that is resistant to kinking.

Each catheter has positioned on its respective distal end a remotely expandable and compliant occlusion device, such as an expandable occlusion mesh or inflatable occlusion or Fogarty balloon (see FIG. 1): an occlusion balloon 6 on the exterior surface of the distal end of the inner catheter 5; and a thrombectomy removal device, here balloon 56, positioned on the exterior surface of the distal end of the outer catheter 10. As will be discussed later, the thrombectomy balloon does not need to be as flexible as the header or occlusion balloon 6. Each balloon catheter contains the tubing and valves (generally a stopcock) associated with each catheter to allow for inflation and deflation of the associated balloon—generally, inflation is accomplished by using a marker fluid (e.g., radio-opaque) supplied by a syringe coupled to the stopcock at a manifold, generally at Y adapter, attached to the proximal or working end of the catheter.

A. Balloon Collared Sheath

The balloon-collared sheath 100 comprises a catheter sheath 60 and an integral balloon-collar 65 mounted near the distal tip of the sheath 60. The catheter sheath 60 will be introduced in to the body generally through a catheter sheath introducer (not shown). Preferably, positioned on the interior proximal end of the sheath, or coupled to the end of the sheath, is a sealing diaphragm valve, flap valve, self sealing homeostasis valve, or other sealing valve 90 to seal against the guidewire, catheter or other device that extends into the interior of the sheath through the seal. The valve is used to seal the opening in the cannula that comprises the sheath. In use, the catheter balloon assembly 3 will preferably be sealingly slidable in the interior of the obturator sheath 60 through the valve 90.

One embodiment of the balloon collared sheath 1 includes a sheath 60 that comprises a cannula eighteen French in size and approximately twenty cm in length. It includes a removable introducer (obturator) with a tapered tip that can be threaded over a guide wire for proper positioning of the sheath 60 inside the vessel (such as a vein or artery) (not shown). The sheath 60 may be made of polyethylene, PTFE ("Teflon"), polyamides or other suitable material, and may be reinforced by a spiral wire incorporated into the wall of the sheath 60. Catheter sheath construction is conventional in the art. Steel wire reinforcement renders the sheath radio-opaque and prevents kinking of the sheath 60 in its passage into the vessel, allowing a smooth curve necessary for passage and manipulation of guide wires and catheters passing through it. The sheath 60 is preferably coated with a hydrophilic substance that eases passage into the vessel in and retards clot formation around it during residence in the vessel. There is an integral balloon collar 65 around the distal end of the sheath (here about at 2.5 cm from the tip). The balloon collar attachment is delineated with radio-opaque markers. The collar 65 can be inflated to occlude the vessel, preventing inflow of blood from "below" the sheath 60 during the thrombectomy process. A radio-opaque fluid is delivered to the collar balloon, such as with a syringe through a side arm (Y branch) of the sheath, controlled by a stopcock or other valve attached to the side arm. The valve 90 at the proximal end of the sheath 60 prevents back bleeding from the vein through the sheath 60 and allows instrumentation, such as guide wires 50 and the dual catheter assembly 3, to be introduced through the valve 90 into the catheter sheath central lumen and manipulated without serious back bleeding through the valve 90.

B. The Catheter Balloon Assembly

As described, the preferred catheter balloon assembly 3 consists of two balloons 5, 56 each mounted near the tip of two preferably hydrophilic coated steel wire reinforced catheters. One embodiment employs a three through five French sized interior catheter, and six French sized exterior catheters. The two catheters 5, 10 are slidable with respect to each other, allowing independent movement of each catheter and the respective attached balloons. The smaller interior catheter 5 is longer than the exterior catheter 10. The catheters incorporate radio-opaque material in their walls to make them visible under fluoroscopy. Each hollow catheter has a fluid delivery channel (generally on the catheter interior) running from the balloon to a side arm of the proximal or working end, where it can be coupled to an inflation fluid, such as delivered via a syringe coupled to a valve (such as a stopcock) on a Y manifold. The injection or withdrawal of fluid allows for inflation or deflation of the associated balloon, such as with radio-opaque fluid. This is usually accomplished via a syringe attached to the end of the side arm, and the internal balloon pressure is maintained by closure of a stopcock or other valve in the side arm. The proximal working end of each catheter is preferably flared slightly and fitted with a plastic flange to prevent fraying and allow fingergrip of the catheter ends for manipulation.

In one embodiment, the balloons 5, 56 are mounted about 5 mm from the distal tip of respective catheter, with the balloon attachment site delineated with radio-opaque markers. The two balloons are made of flexible material suitable an occlusion or Fogarty balloon, such as polyethylene or latex. The balloons may include spaced circumferential ribbing 59 (shown on FIG. 1A) of the exterior balloon wall, for instance, spaced at 3 to 5 mm intervals on an inflated balloon. For use in the lower venous system, the balloons can be inflated to a size of 16-22 mm and assume a sausage shape of approximately 2-4 cm length when inflated. Two separate catheters could be used to deploy the two balloons, but is not preferred, as a second catheter requires an additional entry site.

C. The Suction Module

Shown in FIG. 3 is one embodiment of the suction module 200. It comprises a preferably hydrophilic, hollow steel-reinforced sheath 250, similar to a catheter guide sheath or introducer sheaths. Suitable sizes include 10-18 French. The sheath 250 preferably includes a removable tapered tip obturator (not shown), which can be introduced into the vein over a guidewire. For use in the lower venous system, a sheath length of approximately 20 cm is sufficient. The sheath has an open tip and a single central interior channel. The proximal end of the sheath 250 is attached to a valve 300, such as a stopcock or a large bore (ID 18 French) ball valve, and from thence to a suction source via suction tubing 350. Suction source can be wall suction, for instance, providing 30-100 mm Hg (which is generally available in most medical centers).

Shown connected to the sheath 250 near its back proximal end, in front of the valve 300, is a hollow branch channel 240, such as a Y-manifold, that fluidly connects with the interior of the suction sheath 250. This channel 240 preferably is made of rigid or semi rigid materials, such as plastic or PTFE with imbedded rigid structure (such as steel wires). Located in the interior of the branch channel 240 is a movable means to fragment a clot. The "means to fragment" can include devices to mechanically break up a clot, such as a flexible coil, a brush, an Archimedes' screw or other devices, preferably the means to fragment extends through a sealing valve, such as a homeostasis valve (not shown). The means to fragment should extend out of the proximal rear of the branch channel 240 for manipulation by an operator. For instance, a brush 500 may be a nylon or polyethylene brush connected to a strong narrow (about $^{32}/_{100}$") semi rigid or rigid stem 501 which exits through the proximal end of the side channel through a valve, such as a diaphragm valve. The means to fragment should be sealing advanceable in the branch channel 240 to allow the working end (e.g., the brush) to be advanced into the interior of the sheath 250, preferably advanceable to the distal end of the suction sheath. The extension of the means to fragment that extends out of the side channel 250 may have a bead 509 near the working back end to prevent inadvertent full retraction of the means to fragment into the side channel 240. The end of the means to fragment that exits the branch channel 240 may be connected to a driving motor to rotate the means to fragment when activated (e.g., turn an Archimedes screw embodiment or a rotary brush embodiment of the means to fragment). Alternatively, a handle may be included on working end of the means to fragment to allow an operator to manually rotate and/or advance the means to fragment as needed. As shown, the brush end of the brush is expandable when it enters the main interior of the sheath, and collapsible when retracted into the side channel—if the side channel is large enough, the brush end may not have to be expandable.

When the means to fragment is retracted, the working end (e.g., brush end) is preferably fully contained in the interior of the branch channel 240. In use, the working end of the means to fragment is advanced into the interior of the suction sheath 250. Preferably, the length of the means to fragment will not be long enough to allow it to extend beyond the distal end of the suction sheath 250.

Use of the Device

The use of the device will be described in the lower venous system to remove a clot in the iliac vein. Its' use should not be so restricted, and the following procedure can be modified to accommodate different applications in many different vessels of a patient. For a lower venous application, for instance to remove a clot in the iliac vein, the device can be inserted into the popliteal vein or the femoral vein. Access for both the balloon module 1 and suction module 200 is initially established, for instance, by needle puncturing the chosen vein 2-4 cm apart at an upper location and a lower location under ultrasound guidance using standard Seldinger techniques. A hydrophilic guidewire (standard commercial issue) of suitable size (for instance, 0.032) is introduced into the vein at each access site, and the needles removed.

At the lower puncture location (i.e., closer to the feet), a 10 French standard catheter introducer sheath (such as a Flexor manufactured by Cook, Inc. of Bloomington, Ind.) is introduced into the vein over the guidewire. The introducer sheath may include a sealing diaphragm or check flow valve. The balloon-collared sheath 100 is then placed over the wire through the 10 French sheath into the vein, with the distal end of the sheath (the end with the balloon collar) is positioned in the vein. The sheath 60 of the balloon-collared sheath is positioned such that the balloon collar 65 at the distal end is placed beyond the end of the 10 French sheath, so that the balloon collar 65 can be freely inflated to occlude the vein when desired. Fluoroscopy can be used to assist placement.

At the upper puncture location, the suction module 200 is deployed over the wire into the vein. The largest diameter sheath size that can be accommodated within the vein is preferred. The obturator (or stylet) of the suction sheath 250 is removed through the proximal end of the suction sheath, with the distal end (the end facing the clot) of the suction sheath extending 3-4 cm into the vein. The valve 300 would be removed to allow removal of the obturator.

The balloon collar 65 on the previously inserted balloon-collared sheath 1 is inflated to occlude the vein, preventing flow from below the collar 65 into the clotted venous segment. The smaller inner occlusion balloon catheter 5 of the catheter balloon assembly 3 is also introduced over the lower guide wire, through the balloon-collared sheath 100, and extended into the vein through the clot, with its balloon 6 positioned past the clot. The outer thrombectomy's balloon catheter 10 is then slid over the inner catheter 5, and extended in the vein through the clot, with the thrombosis balloon 56 balloon positioned above the clot, but below the occlusion balloon 6. After proper positioning, the balloons are inflated (collar balloon, occlusion balloon and thrombectomy balloon) under fluoroscopic control. It is preferred that the occlusion balloon be inflated first, then the balloon collar, then the thrombectomy balloon last. See FIG. 4. Stopcocks or valves are used to maintain the pressure and hence inflated size of all balloons. Additionally, the double catheter configuration (i.e., inner and outer catheters) may be inserted as a unit over the guidewire, properly positioning the occlusion and thrombectomy balloons beyond the clot.

After the device is set, the vein segment containing the clot is substantially isolated by the balloon collar 65 and the occlusion balloon 5 (most segments will have smaller vein branches that are not sealed by this procedure). At this point, the surgeon will begin extracting the clot by slowly drawing or retracting the thrombectomy balloon 56 back toward the clot. This is accomplished by pulling on the attached outer catheter 10 and sliding it back over the smaller stationary inner occlusion balloon catheter 5. The procedure should be monitored by fluoroscopy. The inner occlusion balloon catheter 5 should be held in position by securing it from moving by hand during withdrawal or retraction of the outer thrombectomy balloon catheter 10, making sure under fluoroscopy that the occlusion balloon remains stationary.

Figure 4:
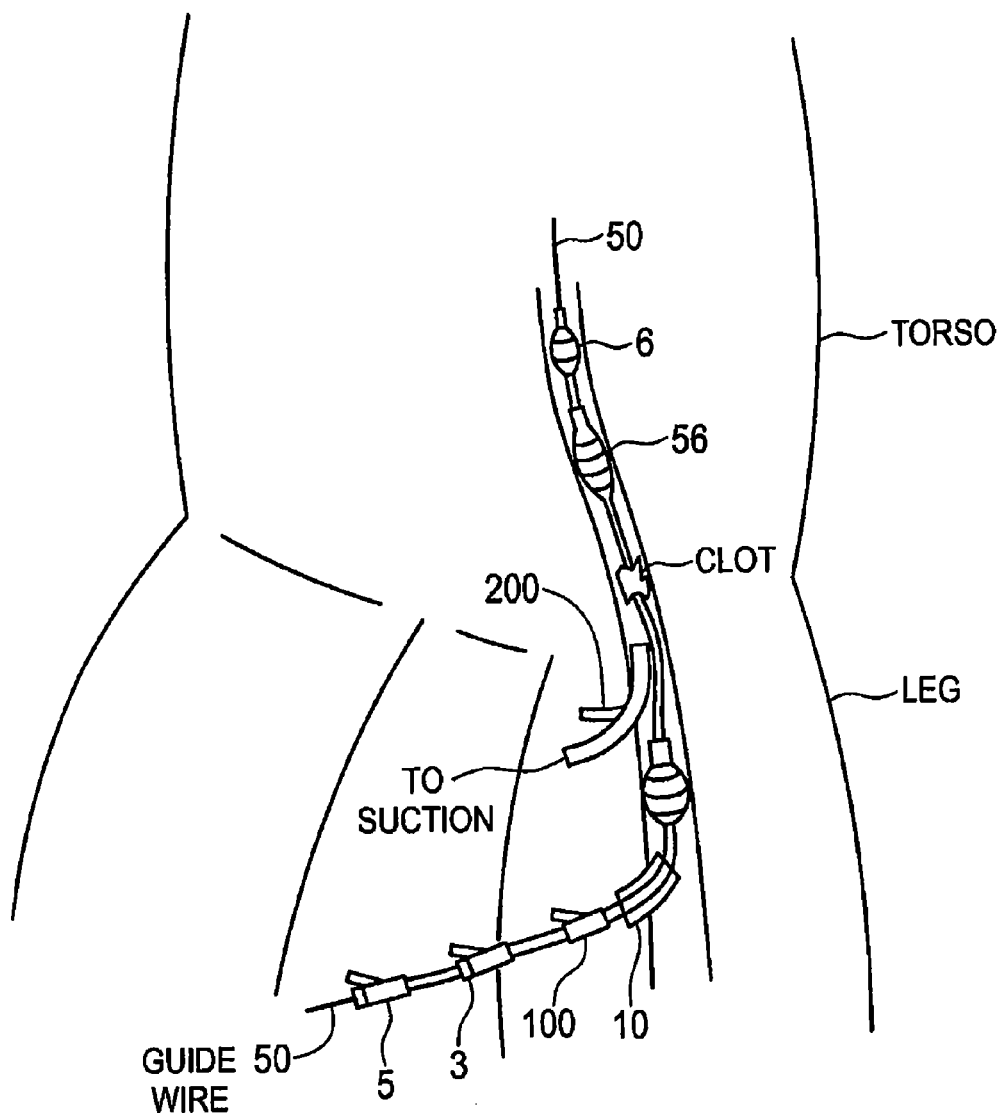
FIG. 4 is a cartoon depiction showing the placement of the modules of the kit within a patient's leg.

The thrombectomy balloon 56, as it is retracted, will come in contact with the clot, and further backward or rearward movement of the thrombectomy balloon 56 will push the clot toward the distal end of the suction sheath 250. The inflation pressure of the thrombectomy balloon 56 is manually varied during this process, where the object is to maintain the exterior surface of the thrombectomy balloon against the interior vessel wall, thereby pushing the clot and gently sliding the balloon against the vessel walls at the same time. When the thrombectomy balloon 56 encounters a clotted region, an increased resistance to balloon withdrawal is encountered. The surgeon will manually adjust the inflation of thrombectomy balloon 56, based upon the manual "feel" of the syringe piston pressure, the resistance felt in retracting the catheter carrying the thrombectomy balloon, and fluoroscopy feedback. The relationship of the kits in use on a patient are depicted in FIG. 4. FIG. 5 depicts the relationship of the suction sheath with respect to the balloon collared.

Suction is initiated through the suction sheath module 200, for instance, preferably using fairly low pressure suction of about 30-50 mm Hg, or higher, as needed. The surgeon will visually evaluate the amount and type of material evacuated by examining the transparent plastic suction tubing and the associated evacuation bottle. If excessive blood loss is noticed, suction can be terminated by closing the associated valve. Note that some blood loss may be expected from venous side channels feeding into the isolated main vein segment. Excessive blood loss generally indicates that the main vein segment is not properly sealed. Failure of seal is generally due to improper inflation of the balloon-collar 65 or the occlusion balloon 5. Irregularities present in the vein wall are generally not a seal issue, as the collar balloon 65 and occlusion balloon 5 are flexible and conformable to the interior cross section of the vein, allowing the balloon to fill and occlude the vein. The surgeon should adjust the pressures in the occlusion balloon 5 and balloon collar 65 to minimize blood loss, at which point suction can then be activated again.

If the interior of the suction sheath 250 clogs up with clot material preventing further evacuation of the thrombectomized clot, the means to fragment the clot, position in the branch channel 240 of the suction sheath module 200 can be extended into the interior of the suction sheath 250 and employed to mechanically break up the clot. For instance, a brush can be pushed up the side channel into the clot and rotated (battery or manually) to break up the clot and clear the blockage allowing the clot to be evacuated by suction.

The thrombectomy procedure is continued till the thrombectomy balloon 56 is close to or touches the tip of the suction sheath 250. Hence, the inner catheter 5 must be longer than the outer catheter 10, to allow retraction of the outer catheter 10 from a position near the inflated and stationary occlusion balloon 6, to the distal end of the suction sheath 250.

At this time, suction is discontinued, and the thrombectomy balloon 56 deflated, one pass has been completed. The deflated thrombectomy balloon 56 may then be repositioned near the stationary occlusion balloon 6 re-inflated, and the procedure repeated. It is preferred that the procedure be repeated until the final two passes are "clean"—with substantially no clot material evacuated.

At this point a venogram or an intravascular ultrasound (IVUS) examination of the thrombectomized venous segment may be carried out to ensure satisfactory clot removal. This is performed by introducing radio-opaque contrast or an IVUS catheter through the suction sheath module 200 after disconnecting the suction tubing from the valve 300. If residual thrombus is still present, suction can be resumed and the process repeated as necessary. If no residual removable thrombus is present, the thrombectomy balloon 56 is deflated and withdrawn outside of the balloon-collared sheath 200. The inflated occlusion balloon 5 may be deflated and removed, or alternatively, the inflated occlusion balloon 5 may be gradually withdrawn over the guide wire, manually controlling the degree of inflation pressure by the syringe during the process, with suction being applied through the suction sheath module 200. Withdrawal of the occlusion balloon 5 in the inflated position ensures extraction of any dislodged clot trapped below this balloon that had not been extracted by the thrombectomy balloon 56.

The occlusion balloon 5 is deflated when it touches the distal end of the suction sheath 250, and then withdrawn through the balloon-collared sheath 200. Preferably, suction is maintained, removing any thrombus lodged between the inflated balloon collar 65 of the balloon-collared sheath 200 and the suction sheath tip. The suction sheath 200 is gradually withdrawn, preferably with on-going suction, until it exits the venous lumen removing any clot still trapped below the suction tip. Suction is then terminated, and the suction sheath is removed, followed by removal of the balloon collar section.

Bleeding from the vein through the sheath entry site is controlled by deploying a closure device, known in the art. The collar balloon 65 of the balloon-collared sheath is then deflated and withdrawn through the 10 French sheath. The 10 French sheath and the guidewire are then removed. A standard closure device is used to control bleeding at the entry site. This completes the procedure.

As described, the balloon catheter 3 assembly is established adjacent to the balloon collared sheath 1 and "below" the clot. The deflated assembly is then pushed through the clot, and inflating the occlusion balloon 5 and thrombectomy balloon 56 "above" the clot, where the inflated thrombectomy balloon 56 is then drawn or pulled toward the distal end of the suction sheath module 200. In some procedures, it may be desired to deploy the balloon catheter assembly 3 distant from the suction, that is, "above" the clot. In this instance, the outer catheter balloon 56 will function as the "occlusion balloon", and the inner catheter balloon 6 will function as the "thrombectomy balloon." The inner balloon 6 would then be pushed forward (as opposed to a retraction or pulling action) into the clot. This generally is not preferred, and a stiff outer catheter should be used to avoid kinking.

Preferably the occlusion balloon is located downstream of the balloon collar, that is, normal fluid flood in the vessel would be from the balloon collar location towards the occlusion balloon. The occlusion balloon and balloon collar substantially remain in place during the procedure to ensure that any clot material that breaks away is isolated between the two balloons during the procedure, thereby preventing an emboli formed from a portion of the clot from moving beyond the isolated vessel segment.

Variations of the device are possible. For instance, other devices can be used in place of the thrombectomy balloon 56. For instance, an expandable compliant cone 58 such as shown in FIG. 6, could be carried on the outer catheter 10 (e.g., deployable through a sheath on the catheter) and the expanded cone used to push the clot toward the suction sheath module 200, such as disclosed in U.S. Pat. No. 7,220,269. Instead of pushing the clot, the present device may also be used to fragment the clot for suction removal. For instance, an expandable plastic or non-fiber brush (preferably sheath deployed) or expandable fiber or non-fibered coiled wire can be carried on the exterior of the outer catheter 10. The expandable brush or expandable coil could be used to fragment the clot for extraction, with suction below the fragmentation site. In this case, the brush, coil or other fragmentation means is preferably positioned "below" the clot, that is, on the side closest to the suction. The occlusion balloon 6 would still be positioned beyond the clot. The catheter balloon assembly includes either a means to fragment a clot (such as a brush, coil, rotatable screw tip, etc.) or a means to mechanically move a clot (e.g., the balloon or expandable cone or other push/pull device). Collectively, these are referred to as a mechanical means to remove a clot.

The present device and its variations may also be used to remove a clot formed in a previously placed stent. For use within a stent, the surgeon may employ more aggressive fragmentation techniques, as the stent wall is much tougher and more difficult to abrade or tear then a vein vessel wall. If an extensive long clot makes it difficult to push or pull the entire clot, the thrombectomy balloon or cone can be deployed in the interior of the clot, clearing the clot below the deployment site, after which, the balloon can be re-deployed behind the clot, to clear the remainder. Finally, the apparatus may also be combined with lysis to assist clot removal.

The invention claimed is:

1. A method of removing a clot comprising the steps of:
   (a) placing a catheter assembly partially in a patients vessel having a clot, where said catheter assembly has a distal and proximal ends, said catheter assembly further comprising a first catheter having proximal and distal ends and carrying a remotely expandable occlusion device near said first catheter distal end and a second catheter having proximal and distal ends and carrying a remotely expandable means for mechanically moving a clot near said second catheter distal end, said first catheter slidable with respect to said second catheter;
   (b) placing a balloon collar sheath partially within said patient's vessel containing a clot where said balloon collar sheath comprises a collar sheath having proximal and distal ends, said balloon collar sheath having an exterior and an open interior, and a sealing valve disposed in said open interior and an inflatable collar balloon disposed on the exterior of said collar sheath;
   (c) placing a suction sheath partially in said patient's vessel having a clot, said suction sheath having proximal and distal ends, said distal end of said suction sheath attachable to a suction means, said suction sheath having proximal and distal ends,
   whereby said occlusion device and said collar balloon are positioned on opposite sides of a clot in a patient's vessel;
   (d) inflating said collar balloon to substantially occlude blood flow around said inflated collar balloon;
   (e) expanding said occlusion device to substantially occlude blood flow around said expanded occlusion device;

(f) positioning said means for mechanically moving a clot near a portion of said clot;
(g) operating said means for mechanically moving a clot;
(h) applying suction to said suction sheath.

2. The method of claim 1 wherein said means for mechanically moving a clot comprises an inflatable thrombectomy balloon, and said step of operating said means for mechanically moving a clot includes the steps of inflating said thrombectomy balloon and moving said inflated thrombectomy balloon from a first position to a second position, where said second position is closer to said suction sheath distal end than said first position.

3. The method of claim 2 wherein said thrombectomy balloon is positioned between said occlusion device and said balloon collar.

4. The method of claim 3 wherein said suction sheath further has a hollow interior, and further comprises a side channel in fluid communication with said hollow interior of said suction sheath, and a clot fragmentation means disposed in said side channel, said clot fragmentation means being movable into said hollow interior of said suction sheath.

5. The method of claim 4 wherein said clot fragmentation means comprises a brush, and said brush is advanced into said interior of said suction sheath at least once after suction is applied.

6. The method of claim 1 further comprising the steps of placing a portion of a suction sheath within a patient's vessel containing a clot, said suction sheath having proximal and distal ends, said suction sheath having an open interior.

7. The method of claim 6 further comprising the step of applying suction to said suction sheath when said clot has been moved to a position adjacent said distal end of said suction sheath.

8. The method of claim 7 wherein said means for mechanically moving a clot comprises an inflatable thrombectomy balloon, and said step of operating said means for mechanically moving a clot includes the steps of inflating said thrombectomy balloon and moving said inflated thrombectomy balloon from a first position to a second position, where said second position is closer to said suction sheath distal end than said first position.

9. The method of claim 8 wherein said thrombectomy balloon is positioned between said occlusion device and said balloon collar.

10. A method of moving a clot comprising the steps of:
(a) placing a catheter assembly partially in a patients vessel having a clot, where said catheter assembly has a distal and proximal ends, said catheter assembly further comprising a first catheter having proximal and distal ends and carrying a remotely expandable occlusion device near said first catheter distal end and a second catheter having proximal and distal ends and carrying a remotely expandable means for mechanically moving a clot near said second catheter distal end, said first catheter slidable with respect to said second catheter;
(b) placing a balloon collar sheath partially within said patient's vessel containing a clot where said balloon collar sheath comprises a collar sheath having proximal and distal ends, said balloon collar sheath having an exterior and an open interior, and a sealing valve disposed in said open interior and an inflatable collar balloon disposed on the exterior of said collar sheath within,
whereby said occlusion device and said collar balloon are positioned on opposite sides of a clot in a patient's vessel;
(c) inflating said collar balloon to substantially occlude blood flow around said inflated collar balloon;
(d) expanding said occlusion device to substantially occlude blood flow around said expanded occlusion device;
(e) positioning said means for mechanically moving a clot near a portion of said clot;
(f) operating said means for mechanically moving a clot.

\* \* \* \* \*